United States Patent

Anderskewitz et al.

[11] Patent Number: 6,127,423
[45] Date of Patent: *Oct. 3, 2000

[54] PHENYLAMIDINE DERIVATIVES, A PROCESS FOR PREPARING THE SAME AND THEIR USE AS MEDICAMENTS

[75] Inventors: Ralf Anderskewitz, Bingen; Kurt Schromm, Ingelheim; Ernst-Otto Renth, Kiel; Franz Birke, Ingelheim; Hans Michael Jennewein, Wiesbaden; Christopher John Montague Meade, Bingen; Andreas Ding, Biberach, all of Germany

[73] Assignee: Boehringer Ingelheim KG, Ingelheim, Germany

[ * ] Notice: This patent is subject to a terminal disclaimer.

[21] Appl. No.: 09/077,900

[22] PCT Filed: Dec. 11, 1996

[86] PCT No.: PCT/EP96/05529

§ 371 Date: Jul. 31, 1998

§ 102(e) Date: Jul. 31, 1998

[87] PCT Pub. No.: WO97/21670

PCT Pub. Date: Jun. 19, 1997

[30] Foreign Application Priority Data

Dec. 13, 1995 [DE] Germany .......................... 195 46 452

[51] Int. Cl.[7] ....................... A61K 31/155; C07C 257/18
[52] U.S. Cl. .................... 514/637; 514/825; 514/826; 514/863; 514/903; 514/908; 560/105; 560/138; 564/47; 564/52; 564/53; 564/116; 564/244

[58] Field of Search .................. 564/47, 52, 53, 564/116, 244; 560/105, 138; 514/637

[56] References Cited

U.S. PATENT DOCUMENTS 5,246,965  9/1993  Main .......................................... 514/532
5,686,496  11/1997 Anderskewitz et al. ................ 514/637

FOREIGN PATENT DOCUMENTS 43 09 285A1  9/1994  Germany .
WO 93/16036  8/1993  WIPO .

OTHER PUBLICATIONS

International Preliminary Examination Report for International Application No. PCT/EP96/05529, Dated Jul. 10, 1998.

*Primary Examiner*—Porfirio Nazario-Gonzalez
*Attorney, Agent, or Firm*—Robert P. Raymond; Alan R. Stempel; Mary-Ellen M. Devlin

[57] ABSTRACT

The invention relates to new phenylamidine derivatives, processes for preparing them and their use as pharmaceutical compositions. The phenylamidines according to the invention correspond to the general formula I

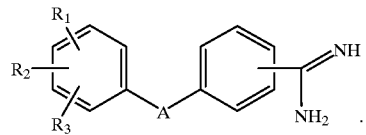

32 Claims, No Drawings

PHENYLAMIDINE DERIVATIVES, A PROCESS FOR PREPARING THE SAME AND THEIR USE AS MEDICAMENTS

The invention relates to new phenylamidine derivatives, processes for preparing them and their use as pharmaceutical compositions. The phenylamidines according to the invention correspond to the general formula I

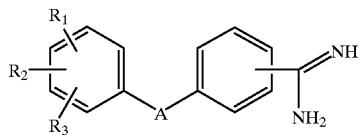

(I)

wherein

A denotes $X_1$—$C_mH_{2m}$—$X_2$—, in which m is an integer 2, 3, 4, 5 or 6 or

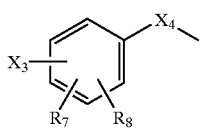

and $X_1$ denotes O, NH or $NCH_3$;
$X_2$ denotes O, NH, $NCH_3$ or

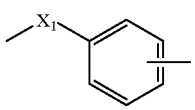

$X_3$ denotes $X_1$—$C_nH_{2n}$ in which n is the integer 1 or 2;
$X_4$ denotes $C_n$—$H_{2n}$—$X_1$, wherein n is the integer 1 or 2;
$R_1$ denotes $C_{5-7}$-cycloalkyl, $Ar_1$, $OAr_1$, $CH_2$—$Ar_2$; $CR_4R_5Ar_3$, $C(CH_3)_2R_6$;
$R_2$ denotes H, $C_{1-6}$-alkyl, OH, halogen, O—$(C_{1-6})$-alkyl;
$R_3$ denotes H, $C_{1-6}$-alkyl;
$R_4$ denotes $C_{1-4}$-alkyl, $CF_3$, $CH_2OH$, COOH, $COO(C_{1-4})$-alkyl;
$R_5$ denotes H, $C_{1-4}$-alkyl, $CF_3$ and
$R_4$ and $R_5$ may also together form a $C_{4-6}$-alkylene group;
$R_6$ denotes $CH_2OH$, COOH, $COO(C_{1-4})$-alkyl, $CONR_9R_{10}$, $CH_2NR_9R_{10}$;
$R_7$ denotes H, halogen, OH, $C_{1-6}$-alkyl or $C_{1-6}$-alkoxy;
$R_8$ denotes H, halogen, OH, $C_{1-6}$-alkyl or $C_{1-6}$-alkoxy;
$R_9$ denotes H, $C_{1-6}$-alkyl, phenyl, phenyl-($C_{1-6}$-alkyl), $COR_{11}$, $COOR_{11}$, CHO, $CONH_2$, $CONHR_{11}$, $SO_2$-($C_{1-6}$-alkyl) $SO_2$-phenyl, wherein the phenyl ring may be mono- or polysubstituted by halogen, $CF_3$, $C_{1-4}$-alkyl, OH, $C_{1-4}$-alkoxy;
$R_{10}$ denotes H or $C_{1-6}$-alkyl and
$R_9$ and $R_{10}$ together may represent a $C_{4-6}$-alkylene group;
$R_{11}$ denotes $C_{1-6}$-alkyl, $C_{5-7}$-cycloalkyl, aryl, heteroaryl, aralkyl or heteroaryl-($C_{1-6}$-alkyl), wherein the aryl or heteroaryl groups may be mono- or polysubstituted by Cl, F, $CF_3$, $C_{1-4}$-alkyl, OH or $C_{1-4}$-alkoxy;
$Ar_1$ denotes an optionally mono- or polysubstituted aryl group, with the exception of the unsubstituted phenyl group and the phenyl group which is monosubstituted by halogen, $C_{1-4}$-alkyl or monosubstituted by $C_{1-4}$-alkoxy;
$Ar_2$ denotes an optionally mono- or polysubstituted aryl group, with the exception of the unsubstituted phenyl group;
$Ar_3$ denotes an optionally mono- or polysubstituted aryl group with the proviso that $R_1$ cannot represent an unsubstituted phenyl group bound via a $C_{1-4}$-alkylene unit;

optionally in the form of the individual optical isomers, mixtures of the individual enantiomers or racemates and in the form of the free bases or the corresponding acid addition salts with pharmacologically acceptable acids.

Preferred compounds according to general formula I are those wherein

A denotes $X_1$—$C_m$—$H_{2m}$—$X_2$ in which m is the integer 2

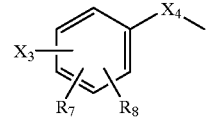

and $X_1$ is O;
$X_2$ is

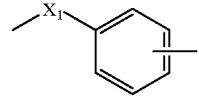

$X_3$ denotes —$X_1$—$C_nH_{2n}$— wherein n is the integer 1 or 2;
$X_4$ denotes —$C_nH_{2n}$—$X_1$— wherein n is the integer 1 or 2;
$R_1$ denotes $C_{5-7}$-cycloalkyl, $Ar_1$, $OAr_1$, $CH_2$—$Ar_2$; $CR_4R_5Ar_3$, $C(CH_3)_2R_6$;
$R_2$ denotes H, $C_{1-6}$-alkyl, OH, Cl, O—$(C_{1-6})$-alkyl;
$R_3$ denotes H, $C_{1-6}$-alkyl;
$R_4$ denotes $C_{1-4}$-alkyl, $CF_3$, $CH_2OH$;
$R_5$ denotes H, $C_{1-4}$-alkyl, $CF_3$, $CH_2OH$ and
$R_4$ and $R_5$ together may also form a $C_{4-6}$-alkylene group;
$R_6$ denotes $CH_2OH$, COOH, $COO(C_{1-4})$alkyl, $CONR_9R_{10}$, $CH_2NR_9R_{10}$;
$R_7$ denotes H, F, Cl, Br, OH, $C_{1-6}$-alkyl or $C_{1-6}$-alkoxy;
$R_8$ denotes H, F, Cl, Br, OH, $C_{1-6}$-alkyl or $C_{1-6}$-alkoxy;
$R_9$ denotes H, $C_{1-6}$-alkyl;
$R_{10}$ denotes H or $C_{1-6}$-alkyl and
$R_9$ and $R_{10}$ together may also represent a $C_{4-6}$-alkylene group;
$Ar_1$ denotes an optionally mono- or polysubstituted aryl group, with the exception of the unsubstituted phenyl group and the phenyl group which is monosubstituted by halogen, $C_{1-4}$-alkyl and monosubstituted by $C_{1-4}$-alkoxy;
$Ar_2$ denotes an optionally mono- or polysubstituted aryl group, with the exception of the unsubstituted phenyl group;

Ar$_3$ denotes an optionally mono- or polysubstituted aryl group
with the proviso that
R$_1$ cannot represent an unsubstituted phenyl group bound via a C$_{1-4}$-alkylene unit;
optionally in the form of the individual optical isomers, mixtures of the individual enantiomers or racemates and in the form of the free bases or the corresponding acid addition salts with pharmacologically acceptable acids.

Particularly preferred compounds of general formula I are those wherein

A denotes

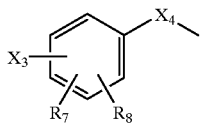

and
X$_1$ is O;
X$_3$ denotes X$_1$—CH$_2$;
X$_4$ denotes CH$_2$—X$_1$;
R$_1$ denotes C$_{5-7}$-cycloalkyl, Ar$_1$, OAr$_1$, CH$_2$—Ar$_2$; CR$_4$R$_5$Ar$_3$, C(CH$_3$)$_2$R$_6$;
R$_2$ denotes H, OH, O—(C$_{1-6}$)-alkyl;
R$_3$ denotes H;
R$_4$ denotes CH$_3$, CH$_2$OH;
R$_5$ denotes H, CH$_3$, CH$_2$OH and
R$_4$ and R$_5$ together may also denote a C$_{4-6}$-alkylene group;
R$_6$ denotes CH$_2$OH, COOH, COO(C$_{1-4}$)-alkyl, CONR$_9$R$_{10}$, CH$_2$NR$_9$R$_{10}$;
R$_7$ denotes H;
R$_8$ denotes H;
R$_9$ denotes H, C$_{1-6}$-alkyl;
R$_{10}$ denotes H or C$_{1-6}$-alkyl and
R$_9$ and R$_{10}$ together may also denote a C$_{4-6}$-alkylene group;
Ar$_1$ denotes an aryl group optionally mono- or polysubstituted by hydroxy or by hydroxy and C$_{1-6}$-alkyl;
Ar$_2$ denotes an aryl group optionally mono- or polysubstituted by hydroxy or by hydroxy and C$_{1-6}$-alkyl;
Ar$_3$ denotes an aryl group optionally mono- or polysubstituted by hydroxy or by hydroxy and C$_{1-6}$-alkyl
optionally in the form of the individual optical isomers, mixtures of the individual enantiomers or racemates and in the form of the free bases or the corresponding acid addition salts with pharmacologically acceptable acids.

Unless specifically stated otherwise, the general definitions are used as follows:

C$_{1-4}$-alkyl, C$_{1-6}$-alkyl and C$_{1-8}$-alkyl, respectively, generally denote a branched or unbranched hydrocarbon group having 1 to 4 or 6 or 8 carbon atoms, which may optionally be substituted by one or more halogen atoms, preferably fluorine, which may be the same or different from one another. The following hydrocarbon groups are mentioned by way of example:

methyl, ethyl, propyl, 1-methylethyl(isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylphenyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise specified, lower alkyl groups having 1 to 4 carbon atoms such as methyl, ethyl, propyl, isopropyl, n-butyl, 1-methylpropyl, 2-methylpropyl or 1,1-dimethylethyl are preferred.

Aryl generally denotes an aromatic group having 6 to 10 carbon atoms, also in compositions in which the aromatic group may be substituted by one or more lower alkyl groups, trifluoromethyl groups, cyano groups, alkoxy groups, nitro groups, amino groups and/or one or more halogen atoms - which may be identical or different; the preferred aryl group is an optionally substituted phenyl group, the preferred substituents being halogen (such as fluorine, chlorine or bromine) and hydroxyl.

Aralkyl generally denotes a C$_{7-14}$-aryl group bound via an alkylene chain, in which the aromatic group may be substituted by one or more lower alkyl groups, alkoxy groups, nitro groups, amino groups and/or one or more halogen atoms, which may be identical or different. Aralkyl groups having 1 to 6 carbon atoms in the aliphatic part and 6 carbon atoms in the aromatic part are preferred.

Unless otherwise stated, the preferred aralkyl groups are benzyl, phenethyl and phenylpropyl or 2-phenyl-isopropyl.

Alkoxy generally represents a straight-chained or branched C$_{1-8}$-hydrocarbon group bound via an oxygen atom. A lower alkoxy group having 1 to 3 carbon atoms is preferred. The methoxy group is particularly preferred.

Unless otherwise stated, amino denotes an NH$_2$ function which may optionally be substituted by one or two C$_{1-8}$-alkyl, aryl or aralkyl groups, which may be identical or different.

Alkylamino represents, by way of example, methylamino, ethylamino, propylamino, 1-methylene-ethylamino, butylamino, 1-methylpropylamino, 2-methylpropylamino or 1,1-dimethylethylamino.

Dialkylamino denotes, for example, dimethylamino, diethylamino, dipropylamino, dibutylamino, di-(1-methylethyl)amino, di-(1-methylpropyl)amino, di-2-methylpropylamino, ethylmethylamino or methylpropylamino.

Cycloalkyl generally denotes a saturated or unsaturated cyclic hydrocarbon group having 5 to 9 carbon atoms which may optionally be substituted by a halogen atom or a number of halogen atoms, preferably fluorine, which may be the same or different. Cyclic hydrocarbon groups having 3 to 6 carbon atoms are preferred. Examples include cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl and cyclononinyl.

Heteroaryl, within the scope of the above definition, generally represents a 5- to 6-membered ring which may contain oxygen, sulphur and/or nitrogen as heteroatoms and onto which another aromatic ring may be fused. 5- and 6-membered aromatic rings which contain an oxygen, a sulphur and/or up to two nitrogen atoms and which are optionally benzocondensed are preferred.

Examples of particular heterocyclic systems include: acridinyl, acridonyl, alkylpyridinyl, anthraquinonyl, ascorbyl, azaazulenyl, azabenzanthracenyl, azabenzanthrenyl, azachrysenyl, azacyclazinyl, azaindolyl, azanaphthacenyl, azanaphthalenyl, azaprenyl, azatriphenylenyl, azepinyl, azinoindolyl, azinopyrrolyl, benzacridinyl, benzazapinyl, benzofuryl, benzonaphthyridinyl, benzopyranonyl, benzopyranyl, benzopyronyl, benzoquinolinyl, benzoquinolizinyl, benzothiepinyl, benzothiophenyl, benzylisoquinolinyl, bipyridinyl, butyrolactonyl, caprolactamyl, carbazolyl, carbolinyl, catechinyl, chromenopyronyl, chromonopyranyl, cumarinyl, cumaronyl, decahydroquinolinyl, decahydroquinolonyl, diazaanthracenyl, diazaphenanthrenyl, dibenzazapinyl, dibenzofuranyl, dibenzothiphenyl, dichromylenyl, dihydrofuranyl, dihydroisocumarinyl, dihydroisoquinolinyl, dihydropyranyl, dihydropyridinyl, dihydropyridonyl, dihydropyronyl, dihydrothiopyranyl, diprylenyl, dioxanthylenyl, oenantholactamyl, flavanyl, flavonyl, fluoranyl, fluoresceinyl, furandionyl, furanochromanyl, furanonyl, furanoquinolinyl, furanyl, furopyranyl, furopyronyl, heteroazulenyl, hexahydropyrazinoisoquinolinyl, hydrofuranyl, hydrofuranonyl, hydroindolyl, hydropyranyl, hydropyridinyl, hydropyrrolyl, hydroquinolinyl, hydrothiochromenyl, hydrothiophenyl, indolizidinyl, indolizinyl, indolonyl, isatinyl, isatogenyl, isobenzofurandionyl, isobenzfuranyl, isochromanyl, isoflavonyl, isoindolinyl, isoindolobenzazapinyl, isoindolyl, isoquinolinyl, isoquinuclidinyl, lactamyl, lactonyl, maleimidyl, monoazabenzonaphthenyl, naphthalenyl, naphthimidazopyridindionyl, naphthindolizinedionyl, naphthodihydropyranyl, naphthofuranyl, naphthyridinyl, oxepinyl, oxindolyl, oxolenyl, perhydroazolopyridinyl, perhydroindolyl, phenanthracquinonyl, phthalideisoquinolinyl, phthalimidyl, phthalonyl, piperidinyl, piperidonyl, prolinyl, parazinyl, pyranoazinyl, pyranoazolyl, pyranopyrandionyl, pyranopyridinyl, pyranoquinolinyl, pyranopyrazinyl, pyranyl, pyrazolopyridinyl, pyridinethionyl, pyridinonaphthalenyl, pyridinopyridinyl, pyridinyl, pyridocolinyl, pyridoindolyl, pyridopyridinyl, pyridopyrimidinyl, pyridopyrrolyl, pyridoquinolinyl, pyronyl, pyrrocolinyl, pyrrolidinyl, pyrrolizidinyl, pyrrolizinyl, pyrrolodioazinyl, pyrrolonyl, pyrrolopyrimidyl, pyrroloquinolonyl, pyrrolyl, quinacridonyl, quinolinyl, quinolizidinyl, quinolizinyl, quinolonyl, quinuclidinyl, rhodaminyl, spirocumaranyl, succinimidyl, sulpholanyl, sulpholenyl, tetrahydrofuranyl, tetrahydroisoquinolinyl, tetrahydropyranyl, tetrahydropyridinyl, tetrahydrothiapyranyl, tetrahydrothiophenyl, tetrahydrothipyranonyl, tetrahydrothipyranyl, tetronyl, thiaphenyl, thiachromanyl, thiadecalinyl, thianaphthenyl, thiapyranyl, thiapyronyl, thiazolopyridinyl, thienopyridinyl, thienopyrrolyl, thienothiophenyl, thiepinyl, thiochromenyl, thiocumarinyl, thiopyranyl, triazaanthracenyl, triazinoindolyl, triazolopyridinyl, tropanyl, xanthenyl, xanthonyl, xanthydrolyl, adeninyl, alloxanyl, alloxazinyl, anthranilyl, azabenzanthrenyl, azabenzonaphthenyl, azanaphthacenyl, azaphenoxazinyl, azapurinyl, azinyl, azoloazinyl, azolyl, barbituric acid, benzazinyl, benzimidazolethionyl, benzimidazolonyl, benzisothiazolyl, benzisoxazolyl, benzocinnolinyl, benzodiazocinyl, benzodioxolanyl, benzodioxolyl, benzopyridazinyl, benzothiazepinyl, benzothiazinyl, benzothiazolyl, benzoxazinyl, benzoxazolinonyl, benzoxazolyl, cinnolinyl, depsidinyl, diazaphenanthrenyl, diazepinyl, diazinyl, dibenzoxazepinyl, dihydrobenzimidazolyl, dihydrobenzothiazinyl, dihydrooxazolyl, dihydropyridazinyl, dihydropyrimidinyl, dihydrothiazinyl, dioxanyl, dioxenyl, dioxepinyl, dioxinonyl, dioxolanyl, dioxolonyl, dioxopiperazinyl, dipyrimidopyrazinyl, dithiolanyl, dithiolenyl, dithiolyl, flavinyl, furopyrimidinyl, glycocyamidinyl, guaninyl, hexahydropyrazinoisoquinolinyl, hexahydropyridazinyl, hydantoinyl, hydroimidazolyl, hydroparazinyl, hydropyrazolyl, hydropyridazinyl, hydropyrimidinyl, imidazolinyl, imidazolyl, imidazoquinazolinyl, imidazothiazolyl, indazolebenzopyrazolyl, indoxazenyl, inosinyl, isoalloxazinyl, isothiazolyl, isoxazolidinyl, isoxazolinonyl, isoxazolinyl, isoxazolonyl, isoxazolyl, lumazinyl, methylthyminyl, methyluracilyl, morpholinyl, naphthimidazolyl, oroticyl, oxathianyl, oxathiolanyl, oxazinonyl, oxazolidinonyl, oxazolidinyl, oxazolidonyl, oxazolinonyl, oxazolinyl, oxazolonyl, oxazolopyrimidinyl, oxazolyl, perhydrocinnolinyl, perhydropyrroloazinyl, perhydropyrrolothiazinyl, perhydrothiazinonyl, perimidinyl, phenazinyl, phenothiazinyl, phenoxathiinyl, phenoxazinyl, phenoxazonyl, phthalazinyl, piperazindionyl, piperazinodionyl, polyquinoxalinyl, pteridinyl, pterinyl, purinyl, pyrazinyl, pyrazolidinyl, pyrazolidonyl, pyrazolinonyl, parazolinyl, pyrazolobenzodiazepinyl, pyrazolonyl, pyrazolopyrimidinyl, pyrazolotriazinyl, pyrazolyl, pyridazinyl, pyridazonyl, pyridopyrazinyl, pyridopyrimidinyl, pyrimidinethionyl, pyrimidinyl, pyrimidionyl, pyrimidoazepinyl, pyrimidopteridinyl, pyrrolobenzodiazepinyl, pyrrolodiazinyl, pyrrolopyrimidinyl, quinazolidinyl, quinazolinonyl, quinazolinyl, quinoxalinyl, sultamyl, sultinyl, sultonyl, tetrahydrooxazolyl, tetrahydropyrazinyl, tetrahydropyridazinyl, tetrahydroquinoxalinyl, tetrahydrothiazolyl, thiazepinyl, thiazinyl, thiazolidinonyl, thiazolidinyl, thiazolinonyl, thiazolinyl, thiazolobenzimidazolyl, thiazolyl, thienopyrimidinyl, thiazolidinonyl, thyminyl, triazolopyrimidinyl, uracilyl, xanthinyl, xylitolyl, azabenzonaphththenyl, benzofuroxanyl, benzothiadiazinyl, benzotriazepinonyl, benzotriazolyl, benzoxadiazinyl, dioxadiazinyl, dithiadazolyl, dithiazolyl, furazanyl, furoxanyl, hydrotriazolyl, hydroxytrizinyl, oxadiazinyl, oxadiazolyl, oxathiazinonyl, oxatriazolyl, pentazinyl, pentazolyl, petrazinyl, polyoxadiazolyl, sydonyl, tetraoxanyl, tetrazepinyl, tetrazinyl, tetrazolyl, thiadiazinyl, thiadiazolinyl, thiadiazolyl, thiadioxazinyl, thiatriazinyl, thiatriazolyl, thiatriazolyl, triazepinyl, triazinoindolyl, triazinyl, triazolinedionyl, triazolinyl, triazolyl, trioxanyl, triphenodioxazinyl, triphenodithiazinyl, trithiadiazepinyl, trithianyl or trioxolanyl.

Particularly preferred heteroaryl groups include, for example, thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

The new compounds may be prepared using the following conventional methods:

1. Reaction of imidoesters of formula II

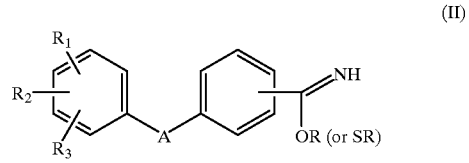

(II)

wherein $R_1$ to $R_4$, A and B are as hereinbefore defined and R preferably denotes a $C_{1-6}$-alkyl group or benzyl (however, the person skilled in the art may also, if desired, use derivatives of other alcohols), and ammonia. The reaction is conveniently carried out in an organic solvent at temperatures between about 0° C. and the boiling temperature of the reaction mixture, preferably between ambient temperature and about 100° C. or boiling temperature, if this is lower. Suitable solvents are polar solvents such as methanol, ethanol and propanol.

If the starting materials are sufficiently acid-stable, the reaction may be carried out via the corresponding acid imide chlorides instead of the imido esters.

2. In order to prepare compounds of formula I wherein A is linked via O or S to at least one of the ring systems: reacting (a) a phenol or thiophenol of formula III

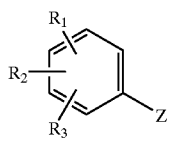

(III)

wherein Z denotes OH or SH and $R_1$, $R_2$ and $R_3$ are as hereinbefore defined, with a compound of general formula IV

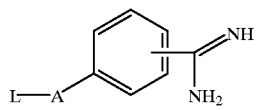

(IV)

wherein A is as hereinbefore defined and L denotes a nucleofugic leaving group, or (b) a phenol or thiophenol of formula V

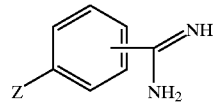

(V)

wherein Z is as hereinbefore defined, with a compound of formula VI:

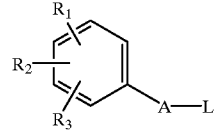

(VI)

wherein A, $R_1$, $R_2$, $R_3$ and L are as hereinbefore defined.

The reaction is carried out in aprotic solvents such as dimethylsulphoxide, dimethylformamide, acetonitrile or alcohols such as methanol, ethanol or propanol using a base (metal carbonate, metal hydroxide, metal hydride) at temperatures between about 0 and 140° C. or the boiling temperature of the reaction mixture.

The phenols or thiophenols may also be used in the form of salts, e.g. the alkali metal salts. The nucleofugic leaving group may be, for example, a halogen such as Br or Cl.

3. Reduction of an amidoxime of formula VII

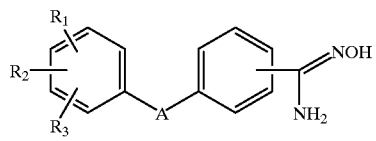

(VII)

wherein A and $R_1$ to $R_3$ are as hereinbefore defined.

Catalytic hydrogenation, particularly with Raney nickel in a lower alcohol such as methanol, is suitable for the step of reducing the amidoxime.

Appropriately, the amidoxime of the formula is dissolved in methanol with the addition of the calculated quantity of the particular acid the salt of which is desired as an end product, and hydrogenated at ambient temperature under slight pressure, e.g. 5 bar, until the uptake of hydrogen has ceased.

The starting materials may be obtained from known compounds by conventional methods.

Thus, the starting materials for process 1 may be obtained from the corresponding nitrites by reacting with HCl via the step of the imide chlorides or directly by reacting with $C_{1-6}$-alcohols or benzyl alcohol, for example, in the presence of an acid such as HCl. Reacting the nitrites with $H_2S$ in solvents such as pyridine or dimethylformamide in the presence of a base such as triethylamine with subsequent alkylation or benzylation also results in compounds of formula II.

Starting from carboxylic acid amides, which moreover correspond to the compounds of formula II by reacting with a trialkyloxonium salt such as triethyloxonium-tetrafluoroborate in a solvent such as dichloromethane, tetrahydrofuran or dioxane at temperatures of between 0 and 50° C., preferably at ambient temperature, compounds of formula II are obtained.

In order to prepare the starting materials of general formula VII, the corresponding amidoximes may be reacted instead of amidines analogously to process 1 or 2, or by analogous reaction of corresponding nitrites, from which the starting materials of general formula VII are finally obtained by the addition of hydroxylamine.

It has been found that the compounds of formula I are characterised by their versatility in therapeutic applications. Particular mention should be made of those applications in which the $LTB_4$-receptor-antagonistic properties play a part. These include, in particular, arthritis, asthma, chronic obstructive lung diseases, e.g. chronic bronchitis, psoriasis, ulcerative colitis, gastro- or enteropathy induced by non-steroidal antiphlogistics, cystic fibrosis, Alzheimer's disease, shock, reperfusion damage/ischaemia, atherosclerosis and multiple sclerosis.

The new compounds may also be used to treat illnesses or conditions in which the passage of cells from the blood through the vascular endothelium into the tissue is of importance (e.g. metastasis) or diseases and conditions in which the combination of $LTB_4$ or another molecule (such as 12-HETE) with the $LTB_4$-receptor affects cell proliferation (such as chronic myeloid leukaemia).

The new compounds may be used in conjunction with other active substances, e.g. those used for the same indications, or with antiallergics, secretolytics, β₂-adrenergics, steroids administered by inhalation, antihistamines and/or PAF-antagonists. They may be administered topically, orally, transdermally, nasally, parenterally or by inhalation.

The activities may be investigated pharmacologically and biochemically using tests such as those described in WO 93/16036, pages 15 to 17, which are thus incorporated herein by reference.

The therapeutic or prophylactic dose is dependent not only on the potency of the individual compounds and the body weight of the patient but also on the nature and gravity of the condition being treated. For oral use the dose is between 10 and 500 mg, preferably between 20 and 250 mg. For administration by inhalation, the dose given to the patient is between about 0.5 and 25, preferably between about 2 and 20 mg of active substance.

Solutions for inhalation generally contain between about 0.5 and 5% of active substance. The new compounds may be administered in conventional preparations, e.g. as tablets, coated tablets, capsules, lozenges, powders, granules, solutions, emulsions, syrups, aerosols for inhalation, ointments and suppositories.

The Examples which follow show some possible formulations for the preparations:

Examples of Formulations

1. Tablets

| Composition: | |
|---|---|
| Active substance according to the invention | 20 parts by weight |
| Stearic acid | 6 parts by weight |
| Glucose | 474 parts by weight |

The ingredients are processed in the usual way to form tablets weighing 500 mg. If desired, the content of active substance may be increased or reduced and the quantity of glucose reduced or increased accordingly.

2. Suppositories

| Composition: | |
|---|---|
| Active substance according to the invention | 1000 parts by weight |
| Powdered lactose | 45 parts by weight |
| Cocoa butter | 1555 parts by weight |

The ingredients are processed in the usual way to form suppositories weighing 1.7 g.

3. Powders For Inhalation

Micronised powdered active substance (compound of formula I; particle size approximately 0.5 to 7 μm) are packed into hard gelatine capsules in a quantity of 5 mg, optionally with the addition of micronised lactose. The powder is inhaled from conventional inhalers, e.g. according to DE-A 33 45 722, to which reference is hereby made.

Example of Synthesis

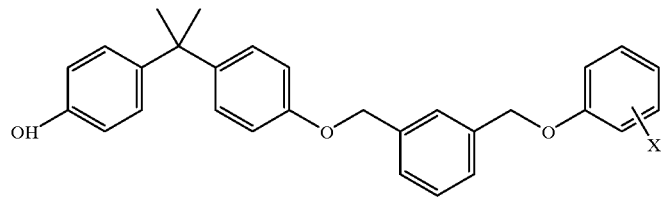

Amidoxime: X=para-C(=NOH)NH₂

2.0 g of the nitrile of the above formula (X=para-CN) are placed in 40 ml of ethanol, refluxed and a mixture of 1 g of Na₂CO₃ in 5 ml of water and 1.24 g of hydroxylamine×HCl is added dropwise. After 5 hours' refluxing the solvent is distilled off, the residue is stirred with 50 ml of water, extracted 3× with 50 ml of ethyl acetate and the combined organic phases are dried. After filtering, the substance is evaporated down in vacuo and the residue is purified by flash chromatography (silica gel 60, CH₂Cl₂/methanol 9:1). The product is dissolved in ethanol, acidified with ethanolic HCl and precipitated as the hydrochloride using ether. The oil obtained is crystallised with ethyl acetate. Yield: 2.0 g of white crystals.

4-[[3-[[4-[1-(4-Hydroxyphenyl)-1-methylethyl]phenoxy]-methyl]phenyl]methoxy]benzolcarboximidamide hydrochloride (X=para-C(=NH)—NH₂)

2.0 g of the amidoxime of the above formula (X=para-C(=NOH)—NH₂) are dissolved in 50 ml of methanol and hydrogenated with 5 g of methanol-moistened Raney nickel with the addition of 1 ml of 20% ammonium chloride solution for 5 hours under normal pressure and at ambient temperature. The nickel is suction filtered and the solution is filtered through kieselguhr. After concentration by evaporation in vacuo, the residue is stirred with 50 ml of water. The crystals are suction filtered and recrystallised twice from ethanol/ether. Yield: 1.0 g of the amidine compound (the above formula, X=para-C(=NH)—NH₂ as hydrochloride, m.p. 234–236° C.

The following compounds are also obtained, inter alia, using this procedure:

| No. | Compound | Salt form | M.p. min [°C.] | M.p. max [°C.] |
|---|---|---|---|---|
| 2 | 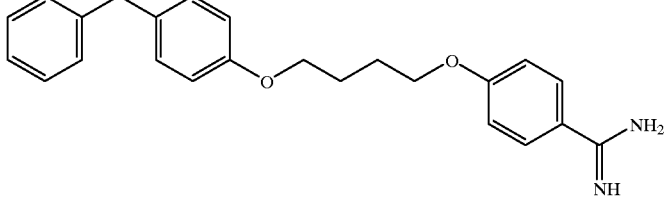 | Chloride | 135 | 140 |
| 3 | 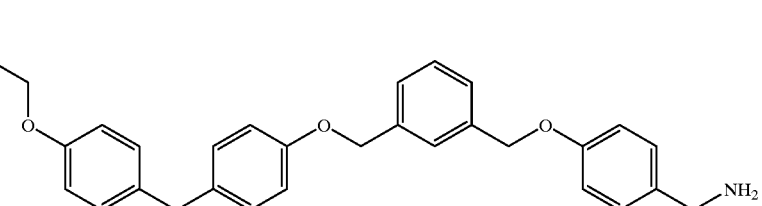 | Chloride | 136 | |
| 4 | 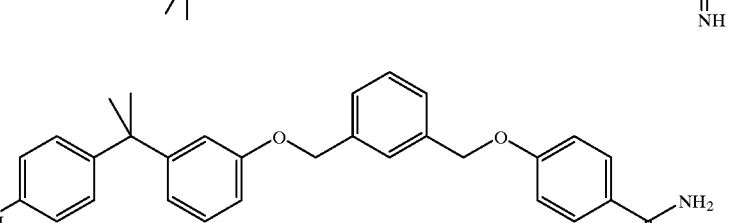 | Fumarate | 199 | 200 |
| 5 | 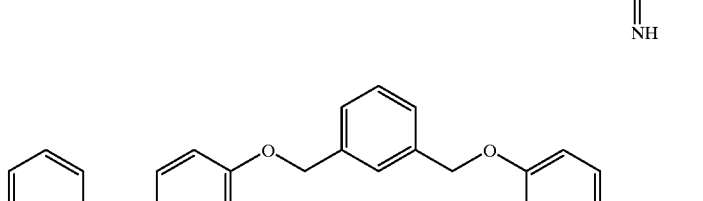 | Methane-sulphonate | 193 | 198 |
| 6 | 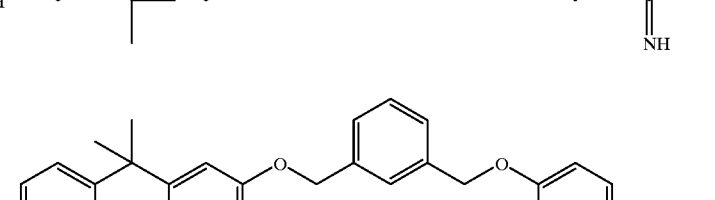 | Methane-sulphonate | 118 | 125 |
| 7 | 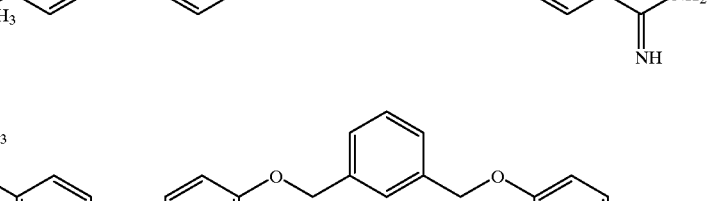 | Chloride | 156 | |

-continued

| No. | Compound | Salt form | M.p. min [°C.] | M.p. max [°C.] |
|---|---|---|---|---|
| 8 | ![compound 8] | Chloride | 218 | 220 |
| 9 | ![compound 9] | Chloride | 130 | 132 |
| 10 | ![compound 10] | Chloride | 117 | 121 |
| 11 | ![compound 11] | Dichloride | 206 | |
| 12 | ![compound 12] | Chloride | 165 | |

-continued

| No. | Compound | Salt form | M.p. min [° C.] | M.p. max [° C.] |
|---|---|---|---|---|
| 13 | | Chloride | 220 | |
| 14 | | Chloride | 172 | 175 |
| 15 | | Chloride | 199 | 275 |
| 16 | | Chloride | 152 | 155 |
| 17 | | Chloride | 186 | 193 |

-continued

| No. | Compound | Salt form | M.p. [°C.] min | M.p. [°C.] max |
|---|---|---|---|---|
| 18 | (1-phenylcyclopentyl-phenoxymethyl-m-phenylene-methyleneoxy-phenyl-amidine) | Chloride | 162 | 165 |
| 20 | (4-fluorophenyl-dimethylmethyl-phenoxymethyl-m-phenylene-methyleneoxy-phenyl-amidine) | Methane-sulphonate | 148 | 154 |
| 21 | (1-phenylcyclohexyl-phenoxymethyl-m-phenylene-methyleneoxy-phenyl-amidine) | Sulphate | 195 | |
| 21 | (phenyl-dimethylmethyl-methoxyphenoxymethyl-m-phenylene-methyleneoxy-phenyl-amidine) | Methane-sulphonate | 153 | 156 |
| 22 | (phenyl-dimethylmethyl-methoxyphenoxymethyl-m-phenylene-methyleneoxy-phenyl-amidine isomer) | Fumarate | 215 | 240 |

-continued
| No. | Compound | Salt form | M.p. min [°C.] | M.p. max [°C.] |
|---|---|---|---|---|
| 23 | 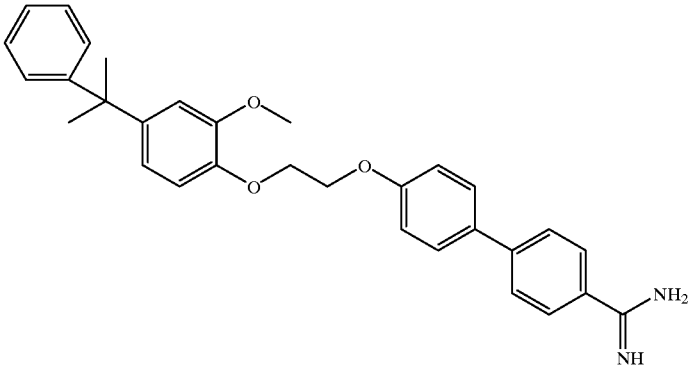 | Methane-sulphonate | 221 | 224 |
| 24 | 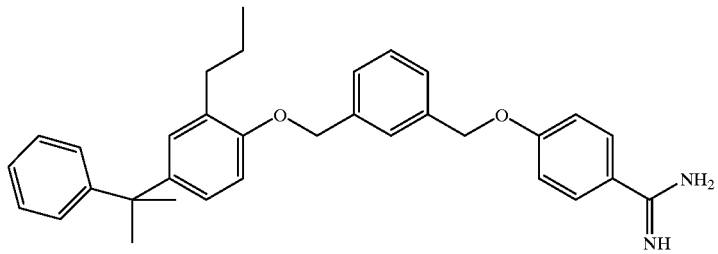 | Sulphate | 217 | |
| 25 | 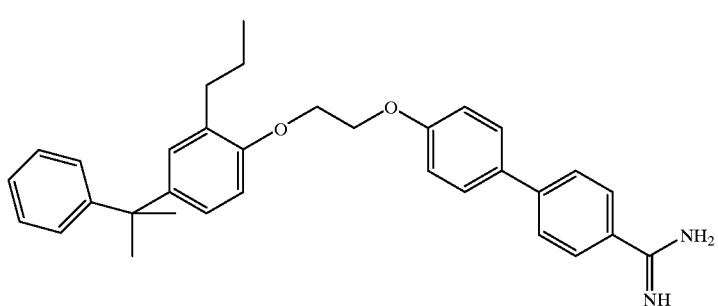 | Methane-sulphonate | 215 | 218 |
| 26 | 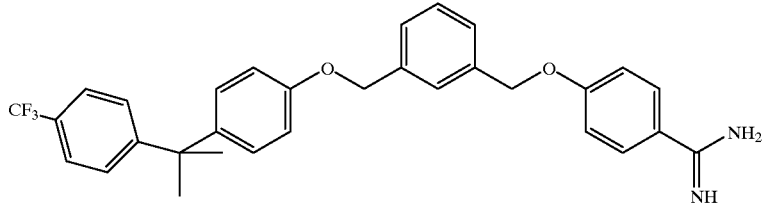 | Methane-sulphonate | 178 | 181 |
| 27 | 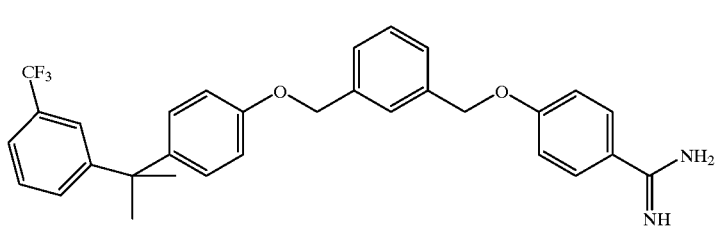 | Methane-sulphonate | 138 | 140 |

-continued

| No. | Compound | Salt form | M.p. min [°C.] | M.p. max [°C.] |
|---|---|---|---|---|
| 28 | | Methane-sulphonate | 123 | 126 |
| 29 | | Chloride | 193 | 196 |
| 30 | | Methane-sulphonate | 133 | 137 |
| 31 | | Fumarate | 225 | |
| 32 | | Sulphate | 230 | |
| 33 | | Methane-sulphonate | 230 | |

-continued

| No. | Compound | Salt form | M.p. [°C.] min | M.p. [°C.] max |
|---|---|---|---|---|
| 34 | (structure) | Methane-sulphonate | 230 | |
| 35 | (structure) | Methane-sulphonate | 230 | 233 |
| 36 | (structure) | Methane-sulphonate | 184 | 187 |
| 37 | (structure) | Methane-sulphonate | 175 | 177 |
| 38 | (structure) | Methane-sulphonate | 160 | 167 |
| 39 | (structure) | Chloride | 258 | 259 |

-continued

| No. | Compound | Salt form | M.p. min [°C.] | M.p. max [°C.] |
|---|---|---|---|---|
| 40 | | Chloride | 212 | 213 |
| 41 | | Fumarate | 219 | 220 |
| 42 | | Fumarate | 257 | |
| 43 | | Furnarate | 211 | 212 |
| 44 | | Furnarate | 258 | 260 |
| 45 | | Furnarate | 224 | 226 |

| [° C.] No. | [° C.] Compound | Salt form | M.p. min | M.p. max |
|---|---|---|---|---|
| 46 | CH₃—SO₂—NH—[structure with two phenyl rings connected via OCH₂-phenyl-CH₂O linker to benzamidine] | Fumarate | 224 | 226 |
| 47 | [diisopropylamide structure connected via phenyl-OCH₂-phenyl-CH₂O-phenyl to amidine] | Fumarate | 216 | |

Surprisingly, the compounds in the Example and in the Table have outstanding $K_i$ values which are largely within the range from 0.2 to 0.7 nmol/l (RB.LTB4/U937 cells).

What is claimed is:

1. A compound of general formula I

[Structure: R₁, R₂, R₃ substituted phenyl connected via A to phenyl with C(=NH)NH₂ group]

wherein

A denotes $X_1$—$C_mH_{2m}$—$X_2$, in which m is an integer 2, 3, 4, 5 or 6 or

[Structure showing X₃, X₄, R₇, R₈ substituted phenyl]

and $X_1$ denotes O, NH or NCH₃;
$X_2$ denotes O, NH, NCH₃ or

[Structure showing X₁ substituted phenyl]

$X_3$ denotes $X_1$—$C_nH_{2n}$ in which n is the integer 1 or 2;
$X_4$ denotes $C_nH_{2n}$—$X_1$, wherein n is the integer 1 or 2;
$R_1$ denotes $C_{5-7}$-cycloalkyl, $Ar_1$, $OAr_1$, $CH_2$—$Ar_2$; $CR_4R_5Ar_3$, or $C(CH_3)_2R_6$;
$R_2$ denotes H, $C_{1-6}$-alkyl, OH, halogen, O—($C_{1-6}$-alkyl);
$R_3$ denotes H, $C_{1-6}$-alkyl;
$R_4$ denotes $C_{1-4}$-alkyl, $CF_3$, $CH_2OH$, COOH, or COO($C_{1-4}$-alkyl);
$R_5$ denotes H, $C_{1-4}$-alkyl, $CF_3$, $CH_2OH$ and
$R_4$ and $R_5$ may also together form a $C_{4-6}$-alkylene group;
$R_6$ denotes $CH_2OH$, COOH, COO($C_{1-4}$-alkyl), $CONR_9R_{10}$, $CH_2N_9R_{10}$;
$R_7$ denotes H, halogen, OH, $C_{1-6}$-alkyl or $C_{1-6}$-alkoxy;
$R_8$ denotes H, halogen, OH, $C_{1-6}$-alkyl or $C_{1-6}$-alkoxy;
$R_9$ denotes H, $C_{1-6}$-alkyl, phenyl, phenyl-($C_{1-6}$-alkyl), $COR_{11}$, $COOR_{11}$, CHO, $CONH_2$, $CONHR_{11}$, $SO_2$—($C_{1-6}$-alkyl), $SO_2$-phenyl, wherein the phenyl ring may be mono- or polysubstituted by halogen, $CF_3$, $C_{1-4}$-alkyl, OH, $C_{1-4}$-alkoxy;
$R_{10}$ denotes H or $C_{1-6}$-alkyl and
$R_9$ and $R_{10}$ together may represent a $C_{4-6}$-alkylene group;
$R_{11}$ denotes $C_{1-6}$-alkyl, $C_{5-7}$-cycloalkyl, aryl, heteroaryl, aralkyl or heteroaryl-($C_{1-6}$-alkyl), wherein the aryl or heteroaryl groups may be mono- or polysubstituted by Cl, F, $CF_3$, $C_{1-4}$-alkyl, OH or $C_{1-4}$-alkoxy;
$Ar_1$ denotes an optionally mono- or polysubstituted aryl group, with the exception of the unsubstituted phenyl group and the phenyl group which is monosubstituted by halogen, $C_{1-4}$-alkyl or monosubstituted by $C_{1-4}$-alkoxy;
$Ar_2$ denotes an optionally mono- or polysubstituted aryl group, with the exception of an unsubstituted phenyl group;
$Ar_3$ denotes an optionally mono- or polysubstituted aryl group with the proviso that $R_1$ cannot represent an unsubstituted phenyl group bound via a $C_{1-4}$-alkylene unit;

optionally in the form of the individual optical isomers, mixtures of the individual enantiomers or racemates and in the form of the free bases or the corresponding acid addition salts with pharmacologically acceptable acids.

2. A compound according to general formula I of claim 1, wherein

A denotes $X_1$—$C_mH_{2m}$—$X_2$ in which m is the integer 2, or

[structure: phenyl ring with $X_3$, $X_4$, $R_7$, $R_8$ substituents]

and
$X_1$ is O;
$X_2$ is

[structure: phenyl ring with $X_1$ substituent]

$X_3$ denotes $X_1$—$C_nH_{2n}$ wherein n is the integer 1 or 2;
$X_4$ denotes $C_nH_{2n}$—$X_1$ wherein n is the integer 1 or 2;
$R_1$ denotes $C_{5-7}$-cycloalkyl, $Ar_1$, $OAr_1$, $CH_2$—$Ar_2$; $CR_4R_5Ar_3$, $C(CH_3)_2R_6$;
$R_2$ denotes H, $C_{1-6}$-alkyl, OH, Cl, O—($C_{1-6}$-alkyl);
$R_3$ denotes H, $C_{1-6}$-alkyl;
$R_4$ denotes $C_{1-4}$-alkyl, $CF_3$, $CH_2OH$;
$R_5$ denotes H, $C_{1-4}$-alkyl, $CF_3$, $CH_2OH$ and
$R_4$ and $R_5$ together may also form a $C_{4-6}$-alkylene group;
$R_6$ denotes $CH_2OH$, COOH, COO($C_{1-4}$alkyl), $CONR_9R_{10}$, $CH_2NR_9R_{10}$;
$R_7$ denotes H, F, Cl, Br, OH, $C_{1-6}$-alkyl or $C_{1-6}$-alkoxy;
$R_8$ denotes H, F, Cl, Br, OH, $C_{1-6}$-alkyl or $C_{1-6}$-alkoxy;
$R_9$ denotes H, $C_{1-6}$-alkyl;
$R_{10}$ denotes H or $C_{1-6}$-alkyl and
$R_9$ and $R_{10}$ together may also represent a $C_{4-6}$-alkylene group;

$Ar_1$ denotes an optionally mono- or polysubstituted aryl group, with the exception of the unsubstituted phenyl group and the phenyl group which is monosubstituted by halogen, $C_{1-4}$-alkyl or monosubstituted by $C_{1-4}$-alkoxy;

$Ar_2$ denotes an optionally mono- or polysubstituted aryl group, with the exception of the unsubstituted phenyl group;

$Ar_3$ denotes an optionally mono- or polysubstituted aryl group with the proviso that $R_1$ cannot represent an unsubstituted phenyl group bound via a $C_{1-4}$-alkylene unit;

optionally in the form of the individual optical isomers, mixtures of the individual enantiomers or racemates and in the form of the free bases or the corresponding acid addition salts with pharmacologically acceptable acids.

3. A compound according to general formula I of claim 1, wherein, p1 A denotes

[structure: phenyl ring with $X_3$, $X_4$, $R_7$, $R_8$ substituents]

and
$X_1$ is O;
$X_3$ denotes $X_1$—$CH_2$;
$X_4$ denotes $CH_2$—$X_1$;
$R_1$ denotes $C_{5-7}$-cycloalkyl, $Ar_1$, $OAr_1$, $CH_2$—$Ar_2$; $CR_4R_5Ar_3$, $C(CH_3)_2R_6$;
$R_2$ denotes H, OH, O—($C_{1-6}$-alkyl);
$R_3$ denotes H;
$R_4$ denotes $CH_3$, $CH_2OH$;
$R_5$ denotes H, $CH_3$, $CH_2OH$ and
$R_4$ and $R_5$ together may also denote a $C_{4-6}$-alkylene group;
$R_6$ denotes $CH_2OH$, COOH, COO($C_{1-4}$-alkyl), $CONR_9R_{10}$, $CH_2NR_9R_{10}$;
$R_7$ denotes H;
$R_8$ denotes H;
$R_9$ denotes H, $C_{1-6}$-alkyl;
$R_{10}$ denotes H or $C_{1-6}$-alkyl and
$R_9$ and $R_{10}$ together may also denote a $C_{4-6}$-alkylene group;

$Ar_1$ denotes an aryl group optionally mono- or polysubstituted by hydroxy or by hydroxy and $C_{1-6}$-alkyl;

$Ar_2$ denotes an aryl group optionally mono- or polysubstituted by hydroxy or by hydroxy and $C_{1-6}$-alkyl with the exception of the unsubstituted phenyl group;

$Ar_3$ denotes an aryl group optionally mono- or polysubstituted by hydroxy or by hydroxy and $C_{1-6}$-alkyl optionally in the form of the individual optical isomers, mixtures of the individual enantiomers or racemates and in the form of the free bases or the corresponding acid addition salts with pharmacologically acceptable acids.

4. A compound of claim 1 selected from the group consisting of the following compounds:

[chemical structure]

where X=para-C(=NH)—NH$_2$
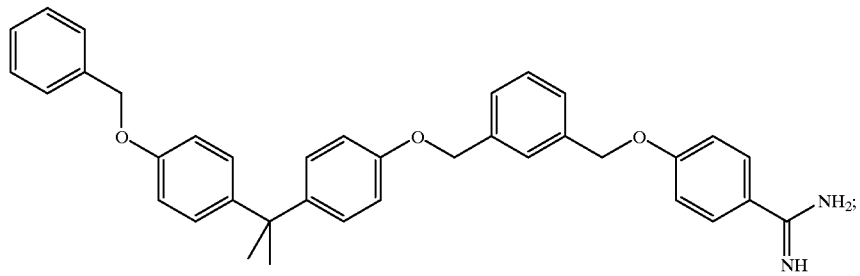
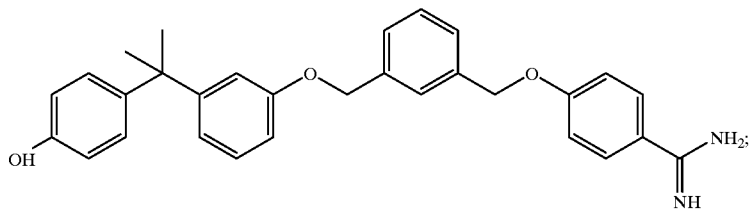
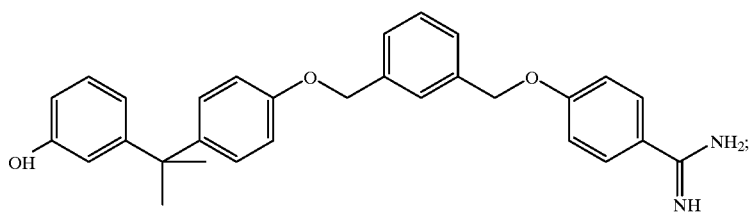
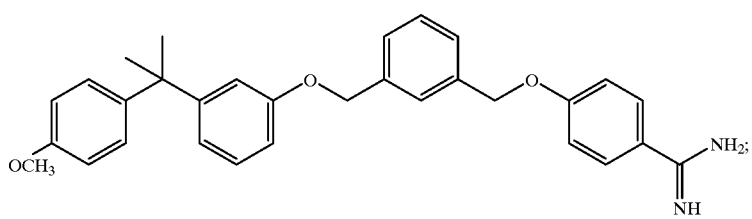
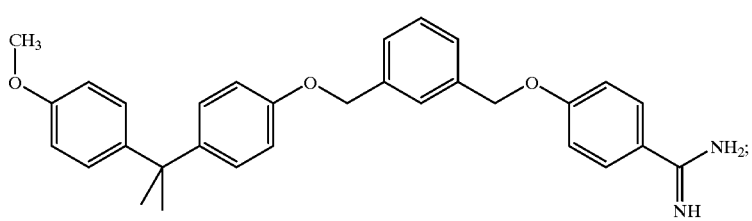
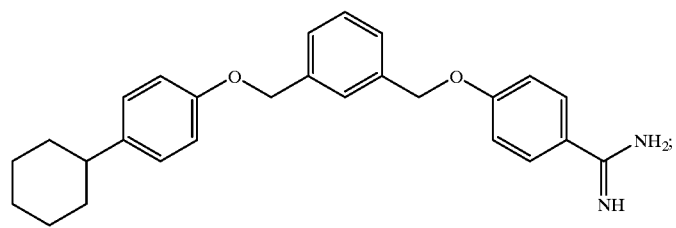

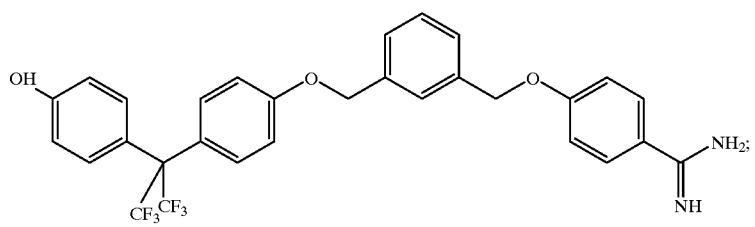
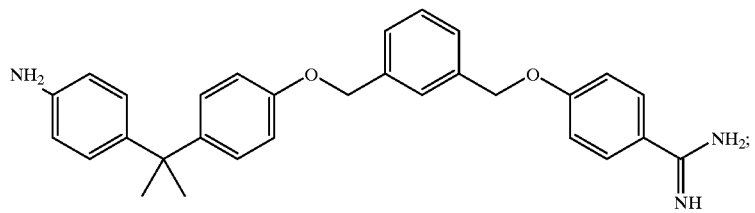
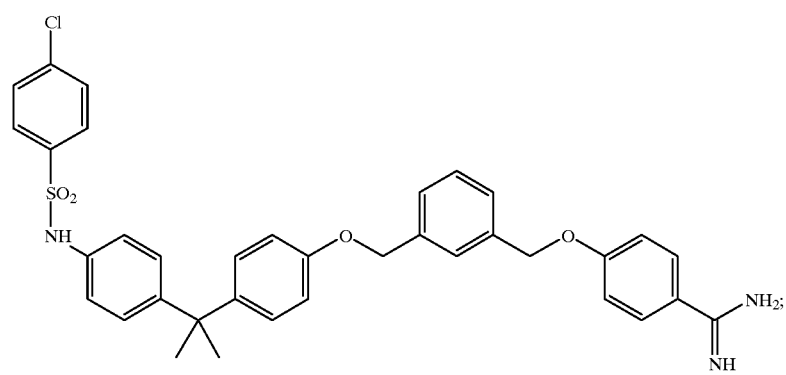
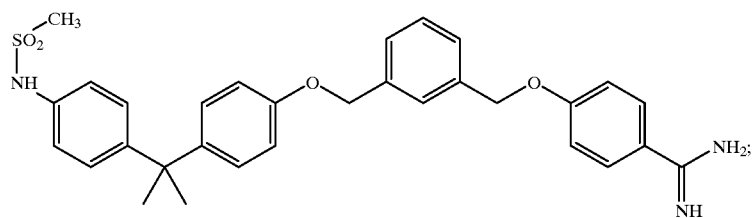
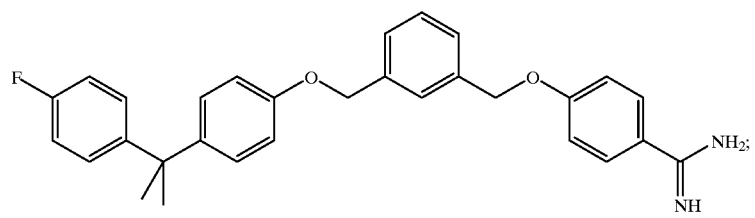
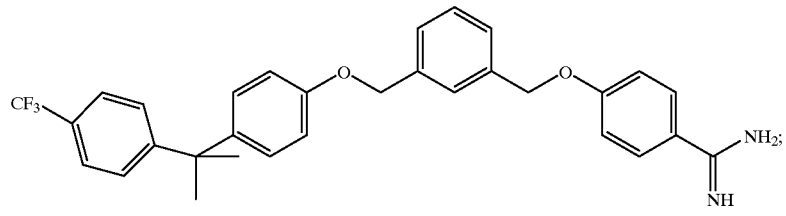
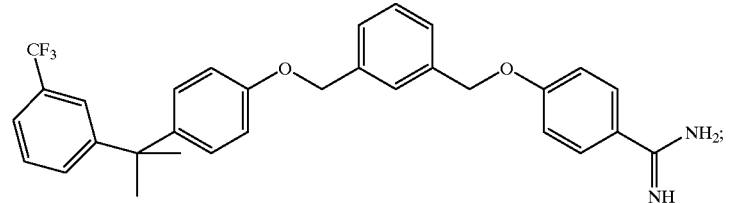

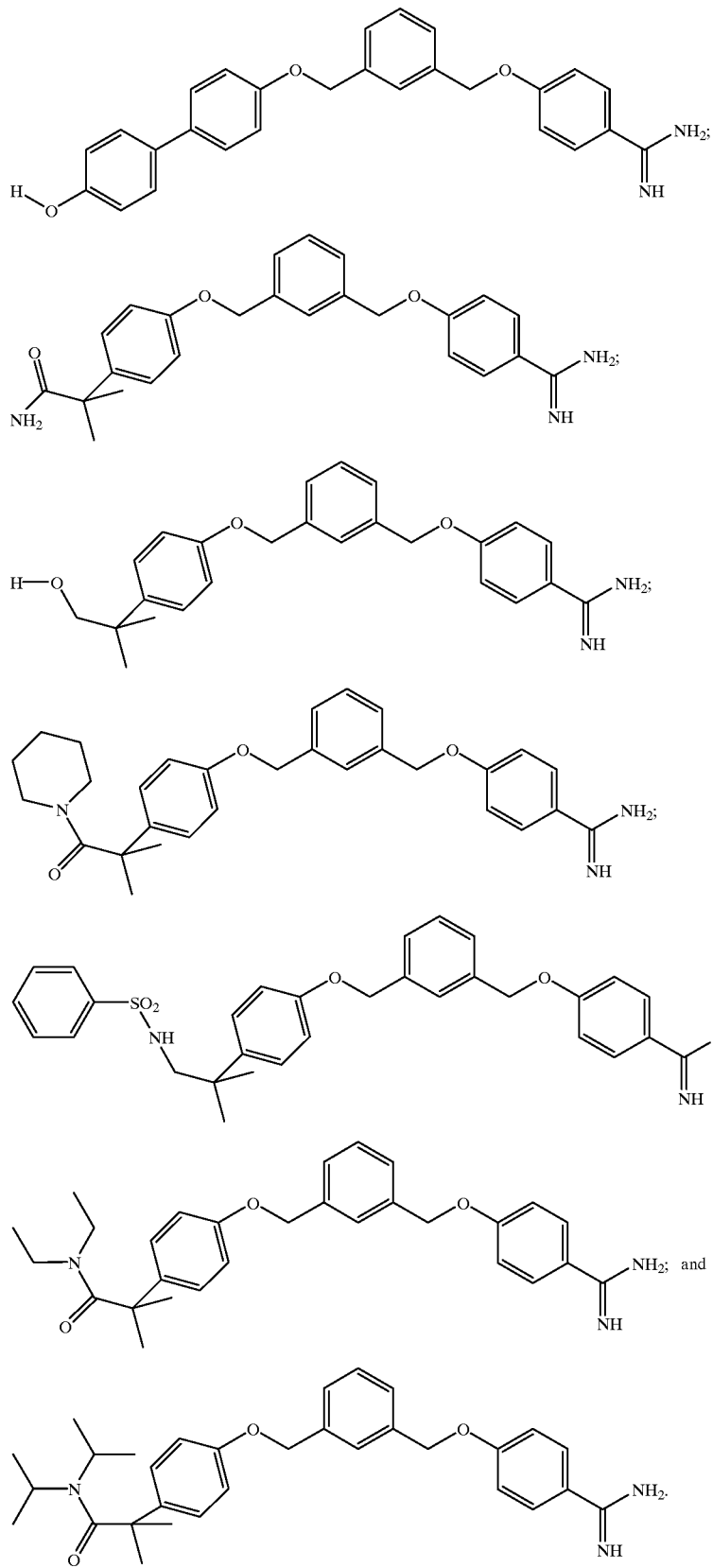

5. A process for preparing a compound according to general formula I of claim 1, wherein an imido ester of general formula II

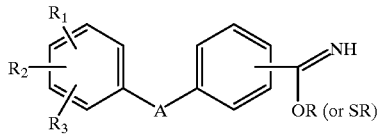

(II)

wherein $R_1$ to $R_3$ and A are defined as in claim 1 and R represents a $C_{1-6}$-alkyl group or benzyl, is reacted with ammonia, in an organic solvent, at a temperature between about 0° C. and the boiling temperature of the reaction mixture.

6. A process according to claim 5, wherein instead of the imido ester of general formula II, the corresponding acid imide chloride is used as starting material.

7. A process for preparing a compound according to general formula I of claim 1 wherein A is linked to at least one of the ring systems via O, wherein a phenol of formula III

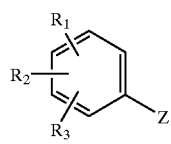

(III)

wherein Z denotes OH and $R_1$, $R_2$ and $R_3$ are as defined in claim 1, is reacted with a compound of general formula IV

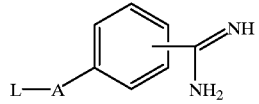

(IV)

wherein A is defined as in claim 1 and L denotes a nucleofugic leaving group, in an aprotic solvent or an alcohol with the addition of a base, at a temperature between 0 and 140° C. or the boiling temperature of the reaction mixture, wherein the phenols of formula III may alternatively be used in the form of their salts.

8. A process for preparing a compound, according to general formula I of claim 1, wherein A is linked to at least one of the ring systems via O, wherein a phenol of general formula V

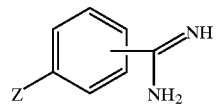

(V)

wherein Z is defined as in claim 6, is reacted with a compound of formula VI

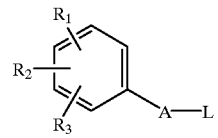

(VI)

wherein A, $R_1$, $R_2$, $R_3$ and L are defined as in claim 6, in aprotic solvents or alcohols with the addition of a base, at a temperature between 0 and 140° C. or the boiling temperature of the reaction mixture, wherein the phenols of general formula V may alternatively be used in the form of their salts.

9. A process for preparing a compound according to general formula I of claim 1, wherein an amidoxime of general formula VII

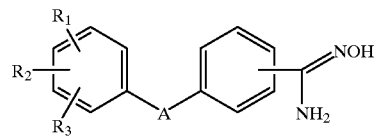

(VII)

wherein A and $R_1$ to $R_3$ are defined as in claim 1, is reduced in an inert polar solvent under elevated pressure.

10. The process of claim 5, wherein the organic solvent is a polar organic solvent.

11. The process of claim 10, wherein the polar organic solvent is methanol, ethanol or propanol.

12. The process of claim 5, wherein the reaction is conducted at a temperature between ambient temperature and about 100° C. or the boiling temperature, if the boiling temperature is lower than 100° C.

13. The process of claim 7, wherein the aprotic solvent is dimethylsulphoxide, dimethylformamide or acetonitrile.

14. The process of claim 7, wherein the alcohol is methanol, ethanol or propanol.

15. The process of claim 7, wherein the base is a metal carbonate, metal hydroxide or metal hydride.

16. The process of claim 7, wherein the phenols of formula III are used in the form of their alkali metal salts.

17. The process of claim 7, wherein the nucleofugic leaving group is a halogen.

18. The process of claim 17, wherein the halogen is Br or Cl.

19. The process of claim 8, wherein the aprotic solvent is dimethylsulphoxide, dimethylformamide or acetonitrile.

20. The process of claim 8, wherein the alcohol is methanol, ethanol or propanol.

21. The process of claim 8, wherein the base is a metal carbonate, metal hydroxide or metal hydride.

22. The process of claim 8, wherein the phenols of formula IV are used in the form of their alkali metal salts.

23. The process of claim 8, wherein the nucleofugic leaving group is a halogen.

24. The process of claim 23, wherein the halogen is Br or Cl.

25. The process of claim 24, wherein the reduction of the amidoxime of general formula VII is by catalytic hydrogenation.

26. The process of claim 25, wherein the reduction of the amidoxime of general formula VII is conducted in the presence of Raney nickel.

27. The process of claim 9, wherein the inert polar solvent is a lower alcohol.

28. The process of claim 27, wherein the lower alcohol is methanol.

29. A pharmaceutical composition comprising a compound according to any one of claims 1 to 3 or the acid addition salts thereof together with convention excipients and carriers.

30. A method for the therapeutic treatment of arthritis, asthma, chronic obstructive lung disease, psoriasis, ulcerative colitis, gastropathy or enteropathy induced by non-steroidal antiphlogistics, cystic fibrosis, Alzheimers's disease, shock, reperfusion damage/ischaemia, atherosclerosis, multiple sclerosis, metastasis or chronic myeloid leukemia, comprising administering a compound according to general formula I of claim 1, or a stereoisomer thereof, or a pharmaceutically acceptable acid addition salt thereof, to a host in need of such treatment.

31. A method for the treatment of a condition responsive to the antagonism of $LTB_4$ receptors which comprises administering to a host in need of such treatment a therapeutically effective amount of a compound according to claim 1.

32. A method according to claim 30, wherein the chronic obstructive lung disease is chronic bronchitis.

\* \* \* \* \*